United States Patent [19]

Chance et al.

[11] 4,421,685
[45] Dec. 20, 1983

[54] PROCESS FOR PRODUCING AN INSULIN

[75] Inventors: Ronald E. Chance, Westfield; James A. Hoffmann, Indianapolis, both of Ind.

[73] Assignee: Eli Lilly and Company, Indianapolis, Ind.

[21] Appl. No.: 262,141

[22] Filed: May 11, 1981

Related U.S. Application Data

[63] Continuation-in-part of Ser. No. 134,390, Mar. 27, 1980, abandoned.

[51] Int. Cl.$^3$ .................. C07C 103/52; C07G 7/00
[52] U.S. Cl. ................................................. 260/112.7
[58] Field of Search ..................................... 260/112.7

[56] References Cited

U.S. PATENT DOCUMENTS 3,420,810 1/1969 Katsoyannis et al. ........... 260/112.7

OTHER PUBLICATIONS

Katsoyannis, Diabetes 13 Jul.–Aug. 1961, 339–348.
Scientia Sinica, 10, 84–104 (1961); 14, 229–236 (1965); 15 544–561 (1966).
Dixon et al., Nature Nov. 26, 1960 721–724.
Kexue Tongbao, (Republic of China) 17 241–277, (1966).
Science, 15, 1509–1514, (1966), Katsoyannis.
Dixon–Symposium 58, pp. 1207–1215 "Recombination of Insulin A and B Chains, Hybrid Insulins and Synthetic Insulin.
Dixon–Biochimica et Biophysica Acta (1962) 483–489.

*Primary Examiner*—Frederick E. Waddell
*Attorney, Agent, or Firm*—William C. Martens; Arthur R. Whale

[57] ABSTRACT

Production of insulin or an insulin analog is provided by combination of an A-chain and a B-chain, which comprises bringing the S-sulfonated form of the A-chain, the S-sulfonated form of the B-chain, and a thiol reducing agent together in an aqueous medium under conditions which produce a mixture having (1) a pH of from about 8 to about 12, (2) a total protein concentration of from about 0.1 to about 50 milligrams per milliliter, and (3) an amount of thiol reducing agent which affords a total of from about 0.4 to about 2.5 —SH groups per each —SSO$_3^-$ group present in the total amount of A- and B-chain S-sulfonates, and allowing formation of insulin or an insulin analog to occur by maintaining the mixture at a temperature of from about 0° C. to about 25° C. and in an environment which provides a source of oxygen.

18 Claims, No Drawings

PROCESS FOR PRODUCING AN INSULIN

CROSS REFERENCE

This is a continuation-in-part of application Ser. No. 134,390, filed Mar. 27, 1980 now abandoned.

BACKGROUND OF THE INVENTION

With the advent of the possibility to generate protein products by recombinant DNA methods and specifically the production of insulin A-chain and insulin B-chain by such techniques [see Goeddel et al., *Proc. Nat'l. Acad. Sci. USA* 76, 106–110 (1979)], the need for an efficient method for combining the A- and B-chains to form insulin has greatly increased.

Typically, the prior art methods for producing insulin by combination of A- and B-chains use as starting materials such A- and B-chains in the form of their stable S-sulfonates. In general, the A- and B-chain S-sulfonates, either separately or together, are reduced to their corresponding —SH compounds, customarily using a large excess of thiol reducing agent. The products are isolated from the reducing medium and, if not reduced together, are brought together in an oxidizing medium, e.g., air, to achieve combination of A- and B-chains with production of insulin. Examples of this methodology are found in Du et al., *Scientia Sinica* 10, 84–104 (1961); Wilson et al., *Biochim. Biophys. Acta* 62, 483–489 (1962); Du et al., *Scientia Sinica* 14, 229–236 (1965); Kung et al., *Scientia Sinica* 15, 544–561 (1966); *Kexue Tongbao* (Republic of China) 17, 241–277 (1966); and Markussen, *J. Acta Paediatrica Scandinavica, Suppl.* 270, 121–126 (1977).

A modification of this approach involves reduction of the A-chain S-sulfonate followed by reaction of the reduced A-chain with B-chain S-sulfonate in an oxidizing atmosphere. See, e.g., Katsoyannis et al., *Proc. Nat. Acad. Sci.* (U.S.A.) 55, 1554–1561 (1966); Katsoyannis, *Science* 154, 1509–1514, (1966); Katsoyannis et al., *Biochemistry* 6, 2642–2655 (1967); U.S. Pat. No. 3,420,810; and Jentsch, *Journal of Chromatography* 76, 167–174 (1973).

Another modification involves partial oxidation of the A-chain —SH compound to produce disulfide formation between the A-6 and A-11 cysteine residues followed by oxidation of the product with B-chain —SH or B-chain S-sulfonate. See, e.g., Belgian Pat. No. 676,069 and Zahn et al., *Liebigs Ann. Chem.* 691, 225–231, (1966).

In each of the above prior art methods, one element is common i.e., the production of insulin by two independent, sequential steps, namely, reduction of S-sulfonate to —SH followed by oxidation to —S—S—.

Dixon et al., *Nature* 188, 721–724 (1960) describe conditions which suggest single solution conversion of A- and B-chain S-sulfonates to insulin using a thiol reducing agent and air oxidation. The details are quite sketchy, and the yield, based only on activity of product recovered, represented 1–2%. However, Dixon, in *Proc. Intern. Congr. Endecrinol.* 2nd London 1964, 1207–1215 (1965), in somewhat further elaboration, suggests, in Table IV at page 1211, that the conditions reported in the earlier publication involve separate reduction and oxidation steps.

In distinction to the above prior art methods, it has now been discovered that it is possible under defined reaction conditions to achieve attractive levels of production of insulins or analogs of insulins from S-sulfonated A- and B-chains by conducting both the reduction and oxidation reactions in a single-step, single-solution process. It is to such a process that this invention is directed.

SUMMARY OF THE INVENTION

Therefore, this invention is directed to a process for combining an A-chain of an insulin or insulin analog and a B-chain of an insulin or an insulin analog to produce an insulin or an insulin analog, which comprises bringing the S-sulfonated form of the A-chain, the S-sulfonated form of the B-chain, and a thiol reducing agent together in an aqueous medium under conditions which produce a mixture having (1) a pH of from about 8 to about 12, (2) a total protein concentration of from about 0.1 to about 50 milligrams per milliliter, and (3) an amount of thiol reducing agent which affords a total of from about 0.4 to about 2.5 —SH groups per each —S—$SO_3$— group present in the total amount of A- and B-chain S-sulfonates; and allowing formation of insulin or an insulin analog to occur by maintaining the mixture at a temperature of from about 0° C. to about 25° C. and in an environment which provides a source of oxygen.

DETAILED DESCRIPTION OF THE INVENTION

As indicated, this invention is directed to an efficient, single-step, single-solution process for producing insulin or an analog of insulin from its constituent S-sulfonated A- and B-chains.

By the term "insulin" is meant, of course, any of the naturally occurring insulins, such as human, bovine, porcine, sheep, fish, avian, and the like, as well as a hybrid formed from a combination of an A-chain of one species and a B-chain of another.

By the term "insulin analog" is meant any of a wide variety of proteins, each of which has the basic A-chain and B-chain containing all of the half-cystine residues in a sequential alignment consistent with that of the natural insulins. The analogs differ from natural insulins by substitution, addition, deletion, or modification of one or more amino acid residues, but with retention of the disulfide bond arrangement and at least a portion of the insulin-like activity. Examples of such analogs are [N-formyl-$Gly^1$-A]insulin, Desamino-$A^1$-insulin, [$Sarcosine^1$-A]insulin, [L-$Alanine^1$-A]insulin, [D-$Alanine^1$-A]insulin, [$Isoasparagine^{21}$-A]insulin, [D-$Asparagine^{21}$-A]insulin, [$Arginine^{21}$-A]insulin, [$Asparagineamide^{21}$-A]insulin, [$Sarcosine^1$-A, $Asparagine^{21}$A]insulin, [$Norleucine^2$-A]insulin, [$Threonine^5$-A]insulin, [$Leucine^5$-A]insulin, [$Phenylalanine^{19}$-A]insulin, [D-$Tyrosine^{19}$-A]insulin, [$Tyrosine^{18}$-A, $Asparagine^{19}$A, $Arginine^{21}$-A]insulin, Des[$B^{28-30}$-tripeptide]insulin, Des[$B^{27-30}$-tetrapeptide]insulin, Des[$B^{26-30}$-pentapeptide]insulin, Des[$B^{27-30}$-tetrapeptide, $Tyrosinamide^{26}$-B]insulin, Des[$B^{26-30}$-pentapeptide, $Phenylalaninamide^{25}$-B]insulin, Des[$B^{1-4}$-tetrapeptide]insulin, Des[$B^{1-5}$-pentapeptide]insulin, [$Lysine^{22}$-B]insulin, [$Leucine^9$-B]insulin, [$Leucine^{10}$-B]insulin, Des[$Phenylalanine^1$-B]insulin, and the like. These and others are described in the literature; see, for example, Blundell, T., et al, *Advances in Protein Chemistry*, 26, 330–362, Academic Press, N.Y., N.Y. (1972); Katsoyannis, P. G., *Treatment of Early Diabetes*, 319–327, Plenum Publishing Corp. (1979); Geiger, R., *Chemiker Zeitung*, Reprint 100, 111–129, Dr. A. Hüthig, Publisher, Heidelberg, W. Germany (1976); Brandenburg, D. et al., *Biochem. J.* 125, 51–52 (1971).

Although the process of this invention is broadly applicable to the production of insulins and insulin analogs, it is highly preferred to use it in the production of naturally-occurring insulins, in particular, human, bovine, or porcine insulins, and most particularly, human insulin.

In carrying out the process of this invention, the combination of A- and B-chain to form insulin or an insulin analog can be achieved over a wide range of ratios of one chain relative to the other. The combination, of course, is inherently limited by the chain, whether A or B, present in the lesser quantity. In any event, although not essential, the customary ratio of A-chain to B-chain, on a weight basis, is from about 0.1:1 to about 10:1. It is highly preferred to carry out the process of this invention using a weight ratio of A-chain to B-chain in the range from about 1:1 to about 3:1. It has also been discovered, within this preferred range, that certain ranges are especially advantageous for production of a particular species of insulin. Thus, in the combinatin of A- and B-chain to produce bovine insulin, it is preferred that the ratio of A-chain to B-chain be within the range of from about 1.4:1.0 to about 1.8:1.0. As to porcine insulin the preferred range is from about 1.0:1.0 to about 1.4:1.0. As to human insulin, the preferred range is from about 1.8:1.0 to about 2.2:1.0.

Another parameter which is significant for carrying out the process of this invention at an optimal level is the protein concentration in the reaction medium. The process can be successfully carried out over a wide range of protein concentrations. Generally, however, the protein concentration will range from about 0.1 to about 50 mg. per ml. of reaction medium. Preferably, the protein concentration will be in the range of from about 2 to about 20 mg. per ml. Again, it has been discovered, within this latter range, that the optimal protein concentration varies depending upon the species of insulin which is produced. Therefore, as to porcine insulin, it is preferred that the protein concentration range be from about 8 to about 16 mg. per ml., whereas, in the production of human or bovine insulin, the preferred range is from about 3 to about 8 mg. per ml.

The process of this invention is carried out in an aqueous medium. The pH of the medium measured at room temperature generally will range from about 8 to about 12. Preferably, it will be from about 9.5 to about 11.0 and optimally will be maintained within the range of from about 10.4 to about 10.6. The pH of the medium may be maintained in the desired range by addition of a suitable buffering agent. Typical such buffering agents are, for example, glycine, glycylglycine, carbonate, tris(hydroxymethyl)aminomethane, N,N-bis(2-hydroxyethyl)glycine, pyrophosphate, N-tris(hydroxymethyl)-methyl-3-aminopropanesulfonic acid, and other like agents which affect pH control within the aforedescribed range. The common and preferred buffering agent is glycine.

The concentration of buffering agent generally ranges from about 0.001 M to about 2 M. Preferably, the concentration is from about 0.01 M to about 1 M, and, most preferably, from about 0.01 M to about 0.1 M.

The A- and B-chains are brought together in the appropriate aqueous medium in the presence of a thiol reducing agent. By "thiol reducing agent" is meant a compound that contains at least one —SH group and has the capacity to effect reduction of the S-sulfonate groups of the A- and B-chains. Although any agent having these characteristics can be employed, a much preferred thiol reducing agent is one which, in its oxidized form, has been cyclized to a highly stable compound. The thiol reducing agent is present in an amount which affords a total of from about 0.4 to about 2.5 —SH groups per each —$SO_3^-$ group present in the total amount of A- and B-chain, and, preferably, from about 0.9 to about 1.1 —SH groups per each $SSO_3^-$ group.

Examples of typical thiol reducing agents are dithiothreitol (DTT), dithioerythritol (DTE), cysteine, 2-mercaptoethanol, methyl thioglycolate, 3-mercapto-1,2-propanediol, 3-mercaptopropionic acid, thioglycolic acid, and other such thiol compounds. Preferred thiol reducing agents are dithiothreitol and dithioerythritol. Another preferred thiol reducing agent is cysteine. Of these, cysteine and dithiothreitol are most preferred.

One of the essential conditions of the process of this invention is that it be carried out in an environment that provides a source of oxygen. This condition can be met merely by permitting the reaction mixture to be open to the air. Although a more direct contact method may be employed, such as, for example, by bubbling air or oxygen into and through the reaction medium, such is not necessary.

In general, therefore, the process of this invention is carried out by preparing a mixture of the A-chain S-sulfonate, the B-chain S-sulfonate, and the thiol reducing agent at desired concentrations in an aqueous medium at a pH of from about 8 to about 12. The mixture, open to air contact, is gently agitated for a period sufficient to allow chain combination to occur, generally at least about 30 minutes. During this period of agitation, the mixture generally is maintained at a temperature of from about 0° C. to about 25° C.; preferably, however, the mixture is subjected to moderate cooling to maintain the temperature at the lower end of this range, generally from about 2° C. to about 10° C.

Once the reaction period has been completed, the insulin or insulin analog product can be isolated by any of a wide variety of methods, all of which are recognized in the field of insulin technology. The most commonly employed techniques for insulin purification are chromatographic techniques. These are readily applicable in recovering insulin from the process of this invention. These can include gel filtration and ion-exchange chromatography.

Moreover, the product can be assayed for purity and activity by recognized methods such as polyacrylamide gel electrophoresis, amino acid analysis, insulin radioreceptorassay, insulin radioimmunoassay, high performance liquid chromatography (HPLC), ultraviolet spectrum, dansylation, rabbit blood glucose assay, and the like.

The insulins which are available from the process of this invention include hybrids comprising the insulin A-chain of one species and the insulin B-chain of another species. The thrust of the process of this invention is directed to a proper combining of A- and B-chain S-sulfonates, and the particular structure of these chains, as long as they truly represent insulin or insulin analog A- and B-chains, is immaterial to the process of this invention.

Although an insulin analog or an insulin hybrid, i.e., an A-chain of one species and a B-chain of another species, can be prepared by the process of this invention, it, of course, is preferred to produce an insulin which is structurally identical to that of a naturally occurring insulin by using an A-chain S-sulfonate and a B-chain S-sulfonate, each of which has the amino acid sequence represented by such insulin. Moreover, it is highly preferred to use the process of this invention to produce porcine, bovine, or human insulin, and most preferably, to produce human insulin.

The insulin or insulin analog A- and B-chains, as already indicated, are available by recombinant DNA methodology. They also can be prepared from natural insulins and by classical peptide synthesis methodology, including either solution or solid phase techniques.

The A- and B-chains are maintained in stable form as S-sulfonates. The S-sulfonate starting materials are available by oxidative sulfitolysis, a treatment by which the A- and B-chains are reacted with sodium sulfite in the presence of a mild oxidizing agent, such as sodium tetrathionate.

As illustrative of the process of this invention, the following examples are provided. These examples are provided for illustrative purposes only, and they are not intended to be limiting upon the scope of this invention.

EXAMPLE 1

Porcine A-chain S-sulfonate (360 mg.) was dissolved in 36 ml. of 0.1 M glycine buffer (pH 10.5), and the pH of the mixture was adjusted to 10.5 with 5 N NaOH. Porcine B-chain S-sulfonate (300 mg.) was dissolved in 30 ml. of 0.1 M glycine buffer (pH 10.5), and the pH of the mixture was adjusted to 10.5 with 5 N NaOH. Dithiothreitol (DTT) (123.4 mg.) was dissolved in 4 ml. of the 0.1 M glycine buffer (pH 10.5), and the pH of the mixture was adjusted to 10.5 with 0.2 ml. of 5 N NaOH.

The A- and B-chain solutions were combined in a 100 ml. vial at room temperature ($\sim 25°$ C.), and 1.91 ml. of the DTT solution then were added to provide an —SH to —$SO_3^-$ ratio of 1.04. The resulting solution was mixed gently in an open beaker with magnetic stirring at 4°–8° C. for 20 hours. Analysis by high performance liquid chromatography (HPLC) indicated an insulin yield of 193.8 mg., or 29% of the total protein.

Forty ml. of this final solution were adjusted to pH 3.15 with acetic acid. The mixture was gel filtered on a 5×200 cm. column of Sephadex G-50 (Superfine) equilibrated and eluted with 1 M acetic acid at 4°–8° C. The insulin peak (elution volume, about 2450–2700 ml.) was pooled and lyophilized with a recovery of 95 mg. of insulin, or 25% of the total protein. The porcine insulin was judged to be quite pure by polyacrylamide gel electrophoresis, amino acid analysis, insulin radioreceptor assay, HPLC, and the rabbit blood glucose reduction test.

EXAMPLE 2

Solutions of bovine A- and B-chain S-sulfonates having a concentration of 5 mg./ml. in 0.01 M glycine buffer (pH 10.5) were prepared. The pH of each was adjusted to 10.5 with 5 N NaOH. DTT (61.7 mg.) was dissolved in 4.0 ml. of 0.1 M glycine buffer (pH 10.5), and the pH was adjusted to 10.5 with 0.15 ml. of 5 N NaOH. To 0.5 ml. of the B-chain solution were added 0.8 ml. of the A-chain solution and 0.035 ml. of the DTT solution at room temperature ($\sim 25°$ C.) to provide an —SH to —$SO_3^-$ ratio of 0.91. The resulting solution was stirred at 4°–8° C. for 20 hours in an open 3-ml. vial. HPLC analysis of the mixture indicated a bovine insulin yield of 1.96 mg., or 30% of the total protein.

EXAMPLE 3

Solutions of porcine A- and B-chain S-sulfonates having a concentration of 10 mg./ml. in 0.1 M glycine buffer (pH 10.5) were prepared. The pH of each was adjusted to 10.5 with 5 N NaOH. DTT (61.7 mg.) was dissolved in 2.0 ml. of glass-distilled water. To 0.5 ml. of the B-chain solution were added 0.6 ml. of the A-chain solution and 29.25 μl. of the DTT solution at room temperature ($\sim 25°$ C.) to provide an —SH to —$SO_3^-$ ratio of 1.00. The resulting solution was stirred at 4°–8° C. in an open 3-ml. vial for 20 hours. HPLC analysis of the mixture indicated a porcine insulin yield of 3.81 mg., or 35% of the total protein.

EXAMPLE 4

Human (pancreatic) B-chain S-sulfonate and several human (pancreatic and E. coli) and porcine (pancreatic) A-chain S-sulfonate solutions having a concentration of 5 mg./ml. in 0.1 M glycine buffer (pH 10.5) were prepared. The pH of each was adjusted to 10.5 with 5 N NaOH. DTT (61.7 mg.) was dissolved in 4.0 ml. of 0.1 M glycine buffer (pH 10.5), and the pH was adjusted to 10.5 with 0.16 ml. of 5 N NaOH. To 1.0 ml of each of the A-chain S-sulfonate solutions were added 0.5 ml. of the B-chain S-sulfonate solution and 0.05 ml. of the DTT solution at room temperature (25° C.) to provide an —SH to —$SSO_3^-$ ratio of 1.09. All solutions were stirred in a chill room (4°–8° C.) in an open vial for 20–22 hours. They then were analyzed by HPLC using a pancreatic human insulin standard for the yield calculations. The results are in the Table following:

TABLE 1

| A-Chain Source | Human Insulin Yield, mg. | % Yield Relative to Total Protein |
|---|---|---|
| Porcine (Pancreatic) | 2.00 | 26.7 |
| Porcine (Pancreatic) | 2.11 | 28.1 |
| Human (Pancreatic) | 1.95 | 26.0 |
| Human (Pancreatic) | 2.03 | 27.1 |
| Human (E. coli) | 1.99 | 26.5 |

EXAMPLE 5

A solution of each of human A- and B-chain S-sulfonates was prepared at a concentration of 5 mg./ml. in a 0.1 M glycine buffer (pH 10.5). The pH of each was adjusted to 10.5 with 5 N NaOH. DTT (61.7 mg.) was dissolved in 4.0 ml. of 0.1 M glycine buffer (pH 10.5), and the pH was adjusted to 10.5 with 0.16 ml. of 5 N NaOH. To 0.5 ml. of the B-chain solution was added at room temperature 1.0 ml. of the A-chain solution followed by 50 μl. of the DTT solution to provide an —SH to —$SSO_3^-$ ratio of 1.09. The resulting solution was stirred at 4°–8° C. in an open 3-ml. vial for 22 hours after which HPLC analysis indicated a human insulin yield of 2.58 mg., or 34% of the total protein.

EXAMPLE 6

Human A-chain S-sulfonate (328 mg.) was dissolved in 65.6 ml. of 0.1 M glycine buffer (pH 10.5), and the pH of the mixture was adjusted to 10.5 with 75 μl. of 5 N NaOH. Human B-chain S-sulfonate (164 mg.) was dissolved in 32.8 ml. of 0.1 M glycine buffer (pH 10.5), and the pH of the mixture was adjusted to 10.5 with 15 μl. of 5 N NaOH. DTT (61.7 mg.) was dissolved in 4.0 ml. of the 0.1 M glycine buffer (pH 10.5), and the pH of the solution was adjusted to 10.5 with 160 μl. of 5 N NaOH.

The A- and B-chain solutions were combined in a 150 ml. glass beaker at room temperature (~25° C.), and 3.28 ml. of the DTT solution were added to provide an —SH to —SSO$_3^-$ ratio of 1.09. The open beaker was placed in an ice-water bath in the chill room and stirred briskly for 30 minutes. The solution was stirred an additional 24 hours in the chill room (4°-8° C.). HPLC analysis at this time indicated a human insulin yield of 148 mg., or 30% of the total protein.

To 100 ml. of this solution were added 25 ml. of glacial acetic acid to a final pH of 3.15. The entire sample was gel filtered on a 5×200 cm. column of Sephadex G-50 (Superfine) equilibrated and eluted with 1 M acetic acid at 4°-8° C. All of the eluted protein was lyophilized. The insulin peak (elution volume 2465-2781 ml.) weighed 125 mg. and represented 29.4% of the recovered protein.

A portion of the above insulin peak (95.5 mg.) was dissolved in about 9 ml. of 0.01 M tris-0.001 M EDTA-7.5 M urea-0.03 M NaCl buffer (pH 8.5 at 4° C.). The mixture was chromatographed through a 2.5×90 cm. DEAE (diethylaminoethyl)-cellulose ion-exchange column equilibrated in the same buffer. The protein was eluted at 4°-8° C. with a gradient of 1 liter each of 0.03 M and 0.09 M NaCl in the same buffer followed by 1 liter of buffer containing 1 M NaCl. Each of the peaks was desalted on Sephadex G-25 (course) columns in 2% acetic acid and lyophilized. The insulin peak (elution volume 878-1008 ml.) weighed 55.73 mg. and represented 84% of the protein recovered.

Zinc insulin crystals were made by dissolving 11.90 mg. of the insulin (DEAE) peak sample in 240 $\mu$l. of 0.1 N HCl followed quickly by 2.16 ml. of a 0.04% ZnCl$_2$-0.05 M sodium citrate-15% acetone solution in a glass centrifuge tube. Crystallization proceeded for 72 hours at room temperature (~25° C.) after which the supernatant was removed, and the crystals were washed twice with cold pH 6.1 water with centrifugation at 2000 rpm at 3° C. between washes. The crystals were redissolved in 0.01 N HCl for analysis.

The resulting human insulin preparation was judged to be quite pure by polyacrylamide gel electrophoresis (a single band), amino acid analysis, insulin radioreceptorassay, insulin radioimmunoassay, HPLC, dansylation and UV spectrum. The USP rabbit assay (144 rabbits) gave a potency of 26.3±1.8 units per mg. (anhydrous).

EXAMPLE 7

Human (*E. coli*) [N-formyl-Gly$^1$] A-chain S-sulfonate and human (pancreatic) B-chain S-sulfonate solutions having a concentration of 5 mg./ml. in 0.1 M glycine buffer (pH 10.5) were prepared. The pH of each was adjusted to 10.5 with 5 N NaOH. DTT (61.7 mg) was dissolved in 4.0 ml. of 0.1 M glycine buffer (pH 10.5), and the pH was adjusted to 10.5 with 0.16 ml. of 5 N NaOH. To 0.5 ml. of the B-chain S-sulfonate solution were added 1.0 ml. of the [N-formyl-Gly$^1$] A-chain S-sulfonate solution and 0.05 ml. of the DTT solution at room temperature (25° C.) to provide an —SH to —S-SO$_3^-$ ratio of 1.10. The solution was stirred in a chill room (4°-8° C.) in an open 3-ml. vial for 23 hours after which HPLC analysis indicated a [N-formyl-Gly$^1$-A] human insulin yield of 1.46 mg., or 19.5% of the total protein.

After acidification to pH 3.15 with glacial acetic acid, a portion of this solution was gel filtered on a 1.5×90 cm. column of Sephadex G-50 (Superfine) equilibrated and eluted with 1 M acetic acid at 4°-8° C. The [N-formyl-Gly$^1$A] human insulin peak (elution volume 87-95 ml.) was pooled, aliquotted and lyophilized. This protein was judged to be quite clean by HPLC and amino acid analysis. The bioactivity of [N-formyl-Gly$^1$-A] human insulin evaluated by radioreceptor assay was 17% relative to a human insulin standard.

EXAMPLE 8

A solution of each of pork A-chain S-sulfonate and human (*E. coli*) B-chain S-sulfonate was prepared at a concentration of 10 mg./ml. in a 0.1 M glycine buffer (pH 10.5). An A-B pool was made using 2 ml. of the A-chain solution for each 1 ml. of the B-chain solution. The A-B pool was adjusted to pH 10.5 with 5 N NaOH. Cysteine (121.2 mg.) was dissolved in 3.0 ml. of 0.1 M glycine buffer (pH 10.5), and the pH was adjusted to 10.5 with 0.35 ml. of 5 N NaOH. To 1.4 ml. of the A-B pool was added at room temperature 52 $\mu$l of the cysteine solution to provide an —SH to —SSO$_3^-$ ratio of 0.95. The resulting solution was stirred at 4°-8° C. in an open 3 ml. vial for 20 hours after which HPLC analysis indicated a human insulin yield of 3.25 mg., or 23.2% of the total protein.

We claim:
1. A process for combining an A-chain of an insulin or an insulin analog and B-chain of an insulin or an insulin analog to produce an insulin or an insulin analog, which comprises bringing the S-sulfonated form of the A-chain, the S-sulfonated form of the B-chain, and a thiol reducing agent together in an aqueous medium under conditions which produce a mixture having (1) a pH of from about 8 to about 12, (2) a total protein concentration of from about 0.1 to about 50 milligrams per milliliter, and (3) an amount of thiol reducing agent which affords a total of from about 0.4 to about 2.5 —SH groups per each —SSO$_3^-$ group present in the total amount of A- and B-chain S-sulfonates, and allowing formation of insulin or an insulin analog to occur by maintaining the mixture at a temperature of from about 0° C. to about 25° C. and in an environment which provides a source of oxygen.

2. Process of claim 1, in which the A-chain S-sulfonate and the B-chain S-sulfonate each has the amino acid sequence represented by a naturally-occurring insulin.

3. Process of claim 2, in which the weight ratio of A-chain S-sulfonate to B-chain S-sulfonate is from about 0.1:1 to about 10:1.

4. Process of claim 3, in which the weight ratio A-chain S-sulfonate to B-chain S-sulfonate is from about 1:1 to about 3:1.

5. Process of claim 4, in which the protein concentration is from about 2 to about 20 milligrams per milliliter.

6. Process of claim 5, in which the pH of the reaction mixture is from about 9.5 to about 11.0.

7. Process of claim 6, in which the pH of the reaction mixture is from about 10.4 to about 10.6.

8. Process of claim 7, in which the thiol reducing agent is present in an amount which affords a total of from about 0.9 to about 1.1 —SH group per each —S-SO$_3^-$ group present in the total amount of A- and B-chain S-sulfonates.

9. Process of claim 8, in which the thiol reducing agent is selected from the group consisting of dithiothreitol and dithioerythritol.

10. Process of claim 9, in which the thiol reducing agent is dithiothreitol.

11. Process of claim 8, in which the thiol reducing agent is selected from the group consisting of cysteine and dithiothreitol.

12. Process of claim 11, in which the thiol reducing agent is cysteine.

13. Process of claim 11, in which the reaction mixture is maintained at a temperature of from about 2° C. to about 10° C.

14. Process of claim 13, in which the insulin that is produced is bovine, porcine, or human insulin.

15. Process of claim 14, in which the insulin that is produced is bovine insulin, the weight ratio of A-chain S-sulfonate to B-chain S-sulfonate is from about 1.4:1.0 to about 1.8:1.0, and the protein concentration is from about 3 to about 8 milligrams per milliliter.

16. Process of claim 14, in which the insulin that is produced is porcine insulin, the weight ratio of A-chain S-sulfonate to B-chain S-sulfonate is from about 1.0:1.0 to about 1.4:1.0, and the protein concentration is from about 8 to about 16 milligrams per milliliter.

17. Process of claim 14, in which the insulin that is produced is human insulin.

18. Process of claim 17, in which the insulin that is produced is human insulin, the weight ratio of A-chain S-sulfonate to B-chain S-sulfonate is from about 1.8:1.0 to about 2.2:1.0, and the protein concentration is from about 3 to about 8 milligrams per milliliter.

* * * * *